United States Patent [19]

Sierocuk et al.

[11] Patent Number: 5,738,628
[45] Date of Patent: Apr. 14, 1998

[54] SURGICAL DISSECTOR AND METHOD FOR ITS USE

[75] Inventors: Thomas J. Sierocuk; Lynetta J. Freeman, both of West Chester; Michel A. Paul, Cincinnati, all of Ohio; Francis J. Kramer, Fort Thomas, Ky.

[73] Assignee: Ethicon Endo-Surgery, Inc., Cincinnati, Ohio

[21] Appl. No.: 409,564

[22] Filed: Mar. 24, 1995

[51] Int. Cl.⁶ ..................................................... A61B 1/00
[52] U.S. Cl. ........................... 600/104; 606/185; 606/190
[58] Field of Search .............................. 600/104; 604/49, 604/164, 165, 264, 170; 606/184, 185, 190

[56] References Cited

U.S. PATENT DOCUMENTS

| | | | |
|---|---|---|---|
| 3,100,482 | 8/1963 | Hett | 128/6 |
| 3,690,769 | 9/1972 | Mori | 356/41 |
| 4,779,611 | 10/1988 | Grooters et al. | 128/4 |
| 5,022,414 | 6/1991 | Muller | 606/190 |
| 5,269,753 | 12/1993 | Wilk | 604/49 |
| 5,271,380 | 12/1993 | Riek et al. | 128/4 |
| 5,309,896 | 5/1994 | Moll et al. | 128/20 |
| 5,334,150 | 8/1994 | Kaali | 604/164 |
| 5,385,572 | 1/1995 | Nobles et al. | 606/185 |
| 5,441,041 | 8/1995 | Sauer et al. | 606/106 |
| 5,540,711 | 7/1996 | Kieturakis et al. | 606/190 X |
| 5,607,441 | 3/1997 | Sierocuk et al. | 606/190 |

FOREIGN PATENT DOCUMENTS

| | | | |
|---|---|---|---|
| 610530 | 6/1978 | U.S.S.R. | 606/190 |
| WO 92/21295 | 12/1992 | WIPO . | |
| WO 93/09722 | 5/1993 | WIPO . | |
| WO 93/24172 | 12/1993 | WIPO . | |

OTHER PUBLICATIONS

Spacemaker™ II Surgical Balloon Dissector, General Surgical Innovations, Inc., Palo Alto, California, 1994.

*Primary Examiner*—Beverly M. Flanagan
*Attorney, Agent, or Firm*—Matthew S. Goodwin; Louis J. Capezzuto

[57] ABSTRACT

A surgical method for creating an operative space during an endoscopic surgical procedure is disclosed. The method incorporates the use of an elongate instrument with an atraumatic tip for facilitating manual dissection of layers of tissues by advancing the instrument between the layers desired to be dissected. As the manual dissection is performed, the space between the dissected layers is enhanced by concurrently insufflating the dissected space as the instrument is advanced. Concurrently insufflating while dissecting eliminates the need to use a balloon dissector for creating the operative space. An improved surgical instrument particularly adapted to carry out this procedure is also disclosed. The improved surgical instrument is an optical obturator incorporating a contrasting imaging element displayed on the transparent tip of the obturator. The contrasting imaging element helps the surgeon to orient the positioning of the instrument relative to adjacent layers desired to be dissected for the creation of the operative space.

9 Claims, 9 Drawing Sheets

SURGICAL DISSECTOR AND METHOD FOR ITS USE

BACKGROUND OF THE INVENTION

This invention relates to a surgical method for creating an operative space endoscopically between attached layers of internal bodily tissue. More particularly, it relates to a surgical method where attached layers of internal bodily tissue are separated, or "dissected", from each other to create the operative space between the separated layers for performing the surgery.

This invention also relates to a surgical instrument for performing the surgical procedure described above to dissect adjacent layers of tissue. Specifically, this invention relates to such an instrument which is adapted for use during an endoscopic surgical procedure.

Endoscopic surgery has become a burgeoning field where operative procedures are carried out through very small openings in the body wall. In contrast to conventional surgical techniques requiring large openings to provide access to the surgical site, the relatively small openings required for endoscopic surgery enable shortened hospital stays and quicker recuperative periods.

In numerous endoscopic procedures, the surgeon requires access to the surgical site. The surgeon must have the ability to introduce required instrumentation through a small incision made in the body wall, and then he often requires the creation of an operative space at the surgical site to carry out the needed procedure.

The instrument which has become the standard in creating a passageway through a small incision in the body wall to provide ingress and egress for surgical instrumentation is the trocar. A conventional trocar includes a cylindrical sleeve having a relatively small diameter, and a puncturing implement, commonly referred to as an "obturator", received through the sleeve for puncturing a small diameter hole through the body wall. When the puncture is made, the obturator is removed from the sleeve, and the sleeve remains in place to provide the requisite passageway for additional instrumentation. In other procedures, the obturator has a rounded, blunt tip instead of a puncturing tip, and the obturator is advanced to enlarge an opening initially made with a scalpel incision.

Recently, advances in the development of trocar design have led to the creation of "optical trocars" which enable the surgeon to visualize the surgical field while the obturator is advanced through tissue. For example, U.S. Pat. No. 5,271,380 (Riek et al., issued Dec. 21, 1993) describes a trocar assembly with an optical obturator consisting of a hollow shaft and a transparent, pointed conical window attached to the shaft distal end. Adjacent the window are optical elements to provide illumination to the surgical field and to transmit images from the illuminated field back to the surgeon. In this way, the surgeon can visualize the surgical field as the optical obturator is advanced through tissue.

Another patent describing a similar trocar assembly including an optical obturator is U.S. Pat. No. 5,334,150 (Kaali, issued Aug. 2, 1994). This patent describes the use of a fully integrated endoscope releasably inserted into and withdrawn from the hollow optical obturator. In the operating room, the endoscope can be connected to a video monitor which captures the illuminated images transmitted from the field as the surgeon advances the obturator through tissue.

Unfortunately, the optical trocars described in these patents were not designed to provide an operative space by dissecting layers of tissue during surgery, but rather to puncture through the body wall to provide a passageway for additional surgical instrumentation. To address the void which has existed for allowing surgeons to create an operative space at a remote site endoscopically, numerous surgical devices and methods have been developed to accomplish this function. U.S. Pat. No. 5,309,896 (Moll et al., issued May 10, 1994) and PCT International Application Nos. WO 93/24172, WO 93/09722 and WO 92/21295 describe surgical devices having an elongated shaft to which is attached an inflatable balloon structure. In one specific procedure, an incision is made adjacent the umbilicus, and the device is advanced between internal layers of bodily tissue until the tip is adjacent the groin. At this point, the balloon is inflated, and the parietal peritoneum, which is a tissue layer lining the contents of the abdomen, is separated from remaining tissue layers to create an operative space. The balloon is thereafter deflated, and the surgeon then has the requisite space available at the site to perform a surgical procedure. One of the procedures which is highlighted in these patents and international publications relates to the surgical repair of a hernia, although other procedures are mentioned as well.

Another interesting patent describing an endoscopic method for surgically repairing a hernia is U.S. Pat. No. 5,269,753 (Wilk, issued Dec. 14, 1993). This patent similarly describes the creation of an operative space at the parietal peritoneum adjacent the groin using an elongate instrument to which is attached an inflatable balloon. Additionally, an endoscope is used to visualize the procedure and the operative space created.

Finally, General Surgical Innovations, Inc. ("GSI") has described a similar balloon device in its recent brochure for the Spacemaker™ Surgical Balloon Dissector. This instrument allows visualization as the instrument is advanced to the proper location for subsequent inflation of the balloon to achieve the required tissue dissection.

Unfortunately, the elongate ballooned instruments, commonly referred to as "balloon dissectors", are inadequate to meet the needs of the surgical community for many reasons. Some of the balloon dissectors are complex to operate, and require several steps which must be performed sequentially. They also require hand-pumping or syringe-filling in order to inflate the balloon. Additionally, the incorporation of the balloon onto the device and the features necessary to make it work properly, add significantly to the cost of these devices.

In view of the deficiencies existing within the surgical community for a simple method and device to dissect internal bodily tissue for the creation of an operative space, unique surgical methods and devices are necessary. Specifically, the surgical community needs a device adapted for endoscopic procedures requiring the dissection of tissue to create an operative space in a simple and cost effective manner.

SUMMARY OF THE INVENTION

In one aspect of the invention, the invention is an improved surgical method for creating an operative space for performing a surgical procedure on a patient. The method of this invention improves on the conventional surgical method. The conventional method incorporates the steps of initially providing an instrument with an elongated shaft and a blunt tip at the shaft distal end, introducing the tip of the instrument adjacent to the first layer of internal bodily tissue desired to be dissected from remaining layers of the tissue, and manually dissecting the first layer from the remaining layers. This manual dissection is performed by advancing the instrument in a direction generally parallel to and between the first layer and the remaining layers so as to create the operative space.

The improvement defining this invention comprises insufflating the operative space concurrently with the step of manually dissecting.

The improved surgical method described above significantly addresses the needs of the surgical community in providing a cost-effective instrument for a simple procedure to create an operative space. The improved method does not require the use of a balloon, and therefore the surgeon does not need to worry about insuring the integrity of the balloon or inflating or deflating the balloon to properly dissect the tissue for the creation of the operative space. Instead, as the layers of internal bodily tissue are dissected by advancing the instrument, the operative space created during the dissection is enhanced by concurrently insufflating the operative space. Insufflation can be provided by introducing a gas, such as carbon dioxide, under positive pressure into the dissected space. Alternatively, other pressurizing fluids can be used. The pressurizing fluid provides the insufflation necessary to enhance the operative space created between the dissected layers, and eliminates the need for inflating and deflating complex and cumbersome balloons.

In a more specific aspect of the surgical method of this invention, the invention is a method for endoscopically dissecting internal bodily tissue to create an operative space remote from a point of entry for performing a surgical procedure on a patient. This method comprises the steps of providing a trocar assembly including a cannula having a cannula housing and an elongate cannula sleeve extending distally from the housing, and an obturator with a blunt tip slidably received into and through the cannula sleeve; making an incision at the point of entry; inserting the blunt tip of the trocar assembly through the incision until the tip contacts a desired layer of the internal bodily tissue; advancing the tip in a direction generally parallel to the desired layer of the internal bodily tissue so as to dissect the desired layer from remaining layers of the tissue while the cannula sleeve of the trocar assembly is likewise advanced; insufflating at and around the dissected layer through the cannula sleeve while continuing to advance the blunt tip and sleeve of the trocar assembly toward a surgical site where the surgical procedure is to be performed; and removing the obturator after the space is created at the surgical site.

In yet another aspect of the invention, the invention is an improved surgical instrument which is particularly adapted to carry out the inventive surgical procedures described above. In particular, the instrument is an improvement over a conventional optical obturator which has an elongated shaft, and a transparent tip extending from the shaft distal end. The shaft and tip share a common longitudinal axis, and the tip is symmetrical about this axis.

The improvement to the conventional optical obturator comprises the incorporation of a contrasting imaging element displayed on the tip and intersecting the common longitudinal axis.

The incorporation of the contrasting imaging element onto the transparent tip of the optical obturator further facilitates the dissection of adjacent layers of bodily tissue during an endoscopic surgical procedure to create an operative space. This is so because the contrasting imaging element provides the surgeon with the critical understanding of the positioning of the instrument relative to the adjacent layers of internal bodily tissue as the instrument is advanced. In other words, it provides the surgeon with the proper orientation of the instrument as it is advanced, insuring that the desired dissection between layers of tissue is being performed properly.

The surgical methods of this invention can be used in any procedures requiring the creation of an operative space for performing a surgical procedure endoscopically. Particularly well suited for the application of this method are procedures such as hernia repair and bladder neck suspension (bladder neck suspension is used for treatment of urinary stress incontinence). The surgical instrument of this invention, while it is particularly adapted for use during endoscopic surgical procedures, can be used in any procedure, open or endoscopic, which can benefit from its enhanced features.

DETAILED DESCRIPTION OF THE PREFERRED EMBODIMENT

Figure 1:
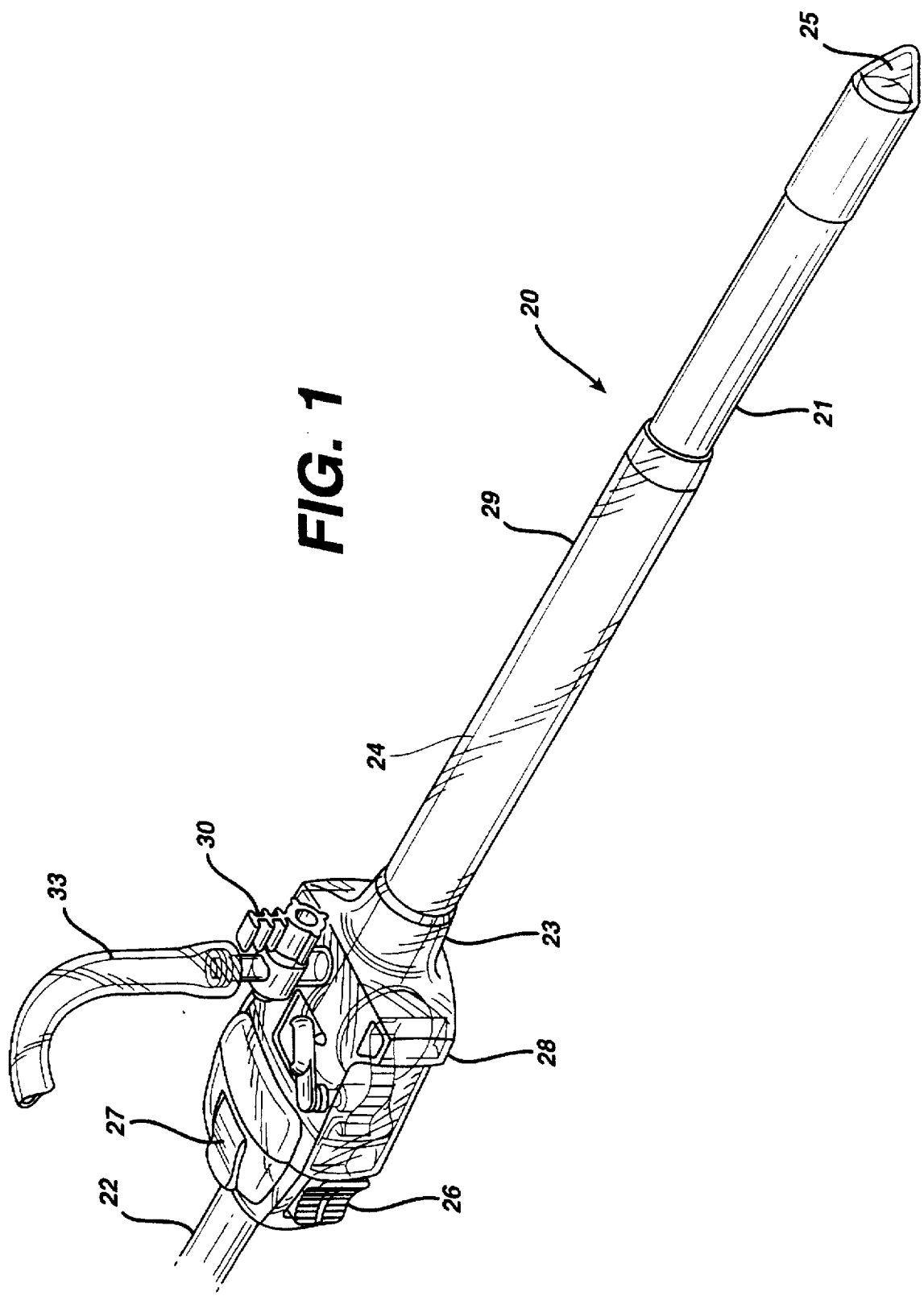
FIG. 1 is a perspective view of a trocar assembly including the surgical instrument of this invention.
Figure 2:
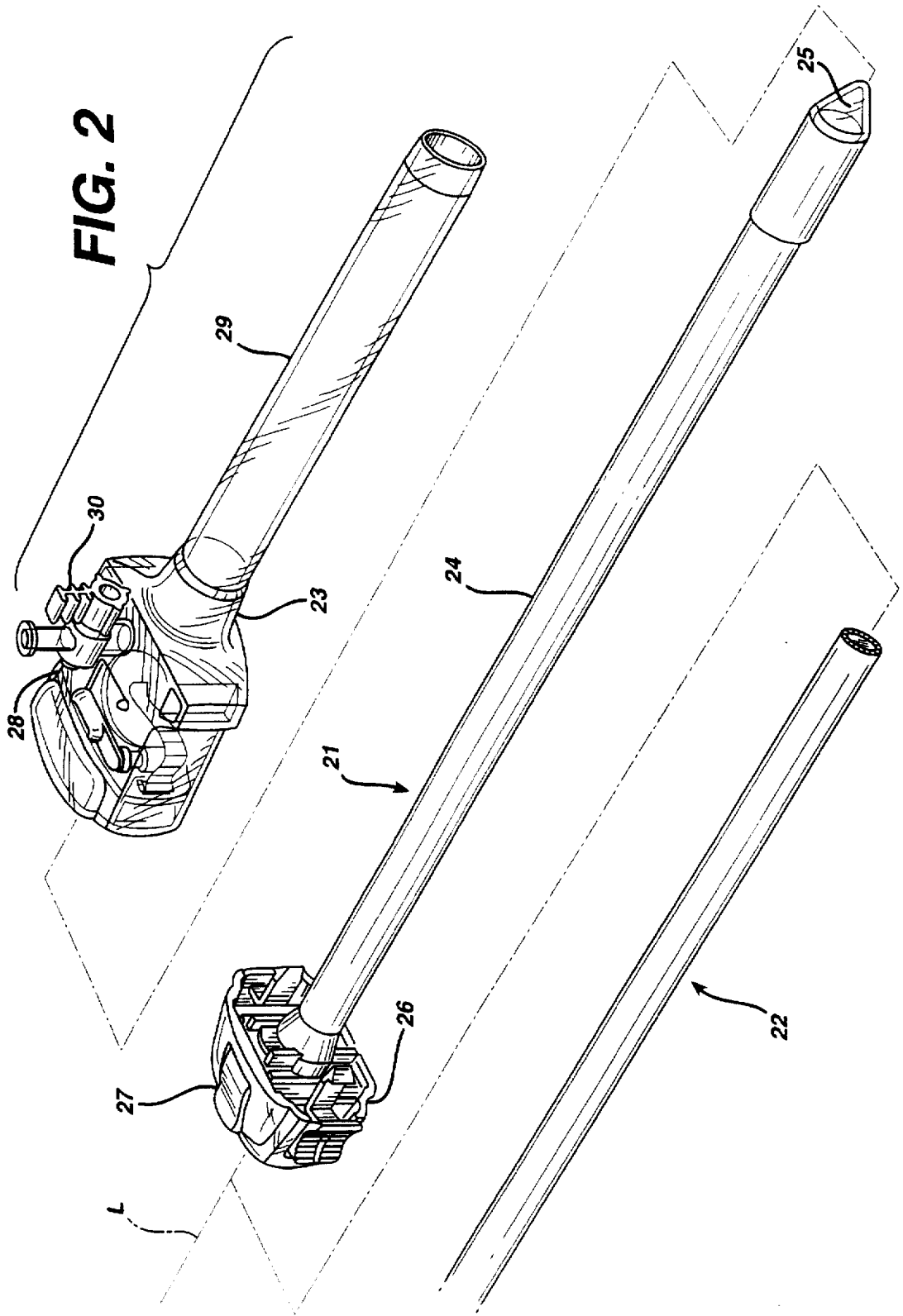
FIG. 2 is an exploded perspective view of the trocar assembly.
Figure 3:
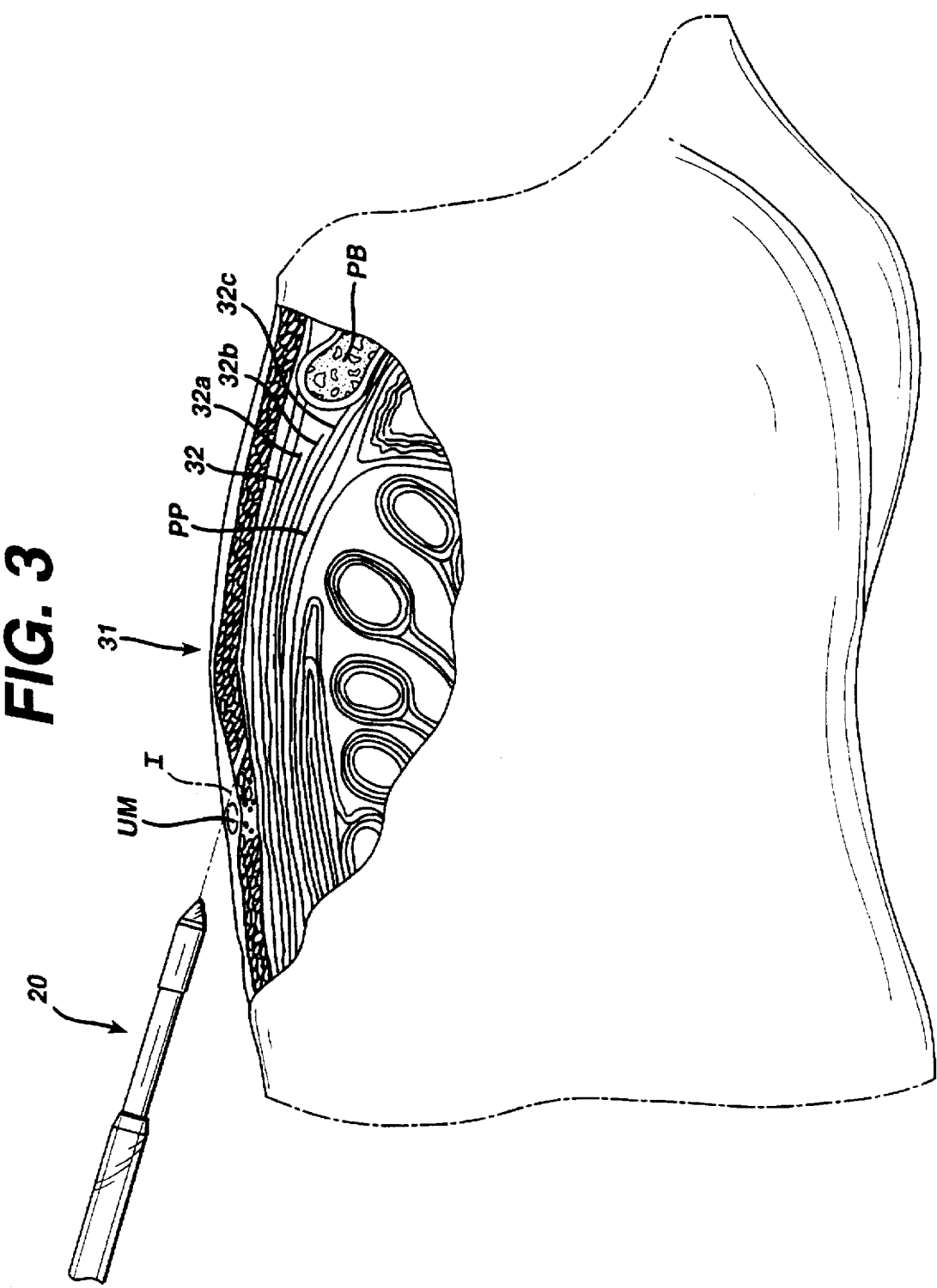
FIGS. 3–8 are a side view and partial cross-section showing the surgical method for creating an operative space on a patient.
Figure 4:
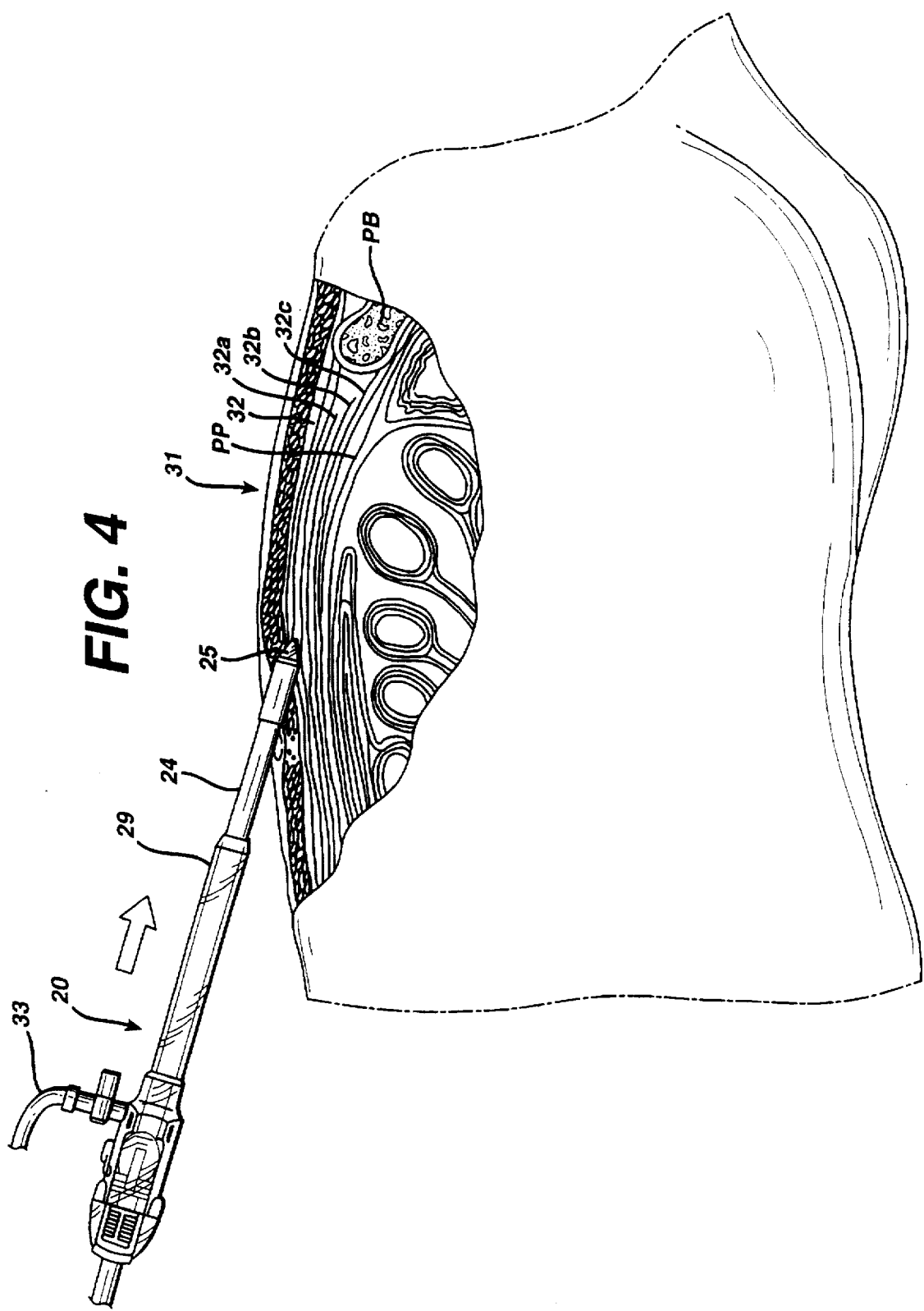

The trocar assembly which is preferably used to dissect adjacent layers of internal bodily tissue for the creation of an operative space while concurrently visualizing the dissection is illustrated in FIGS. 1 and 2. The trocar assembly 20 has three primary components. The primary components of the trocar assembly are the optical obturator 21, endoscope 22, and trocar cannula 23.

Figure 9:
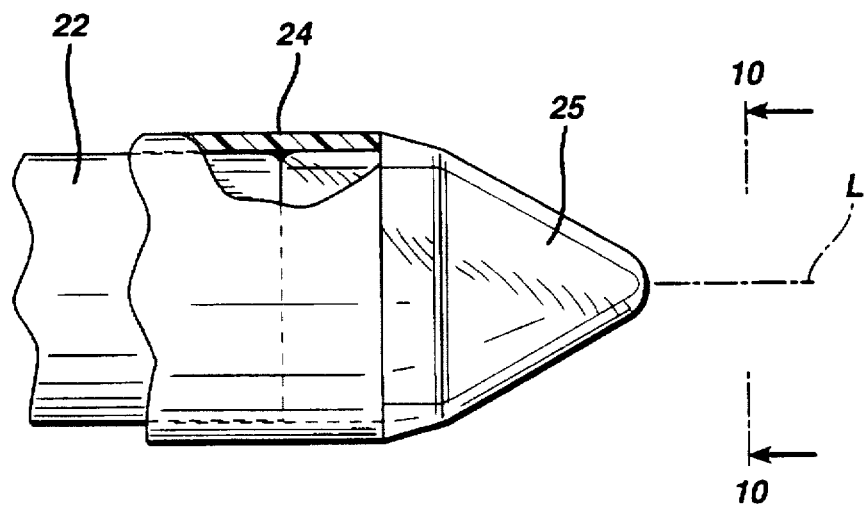
FIG. 9 is a plan view of the shaft distal end and tip of the surgical instrument of this invention.

The optical obturator has an elongated hollow shaft 24. Extending from the shaft distal end is a hollow, transparent blunt tip 25. The tip is in the form of a transparent conical window made from a plastic or glass and has a blunt apex for providing atraumatic dissection of the tissue as the obturator is advanced into and through the tissue. The elongated shaft 24 and transparent tip 25 of the obturator share a common longitudinal axis designated as "L" in FIGS. 2 and 9. The conical tip 25 is symmetrical about longitudinal axis, L.

The endoscope 22 is preferably a conventional, fully-integrated rigid endoscope which can deliver light into the body cavity from an external source of illumination, and can transmit illuminated images from the body cavity to the user onto an eye piece or a video monitor, whichever is desirable. The endoscope during use of the trocar assembly is inserted into and through the elongated hollow shaft 24 of obturator 21 until it is adjacent the transparent tip 25 (see FIG. 9). Therefore, when a light source is activated (not shown), light is emitted from the distal end of the endoscope through the optical window 25 and transmitted images from the body cavity are likewise transmitted through the optical window into and through the endoscope to provide illuminated images of the body cavity for the user of the trocar assembly 20.

The trocar cannula 23 is a conventional trocar cannula including a cannula housing 28 and a cannula sleeve 29 extending from the housing. The optical obturator cooperates with the cannula 23 and the sleeve 29 is sized to allow slidable insertion of the shaft 24 of the obturator into and through not only the cannula housing 28 but also the cannula sleeve 29. The cannula also includes a stop-cock valve 30 for allowing and preventing the passage of an insufflation fluid, e.g. carbon dioxide, through flexible tubing 33 into a portion of the cannula housing 28 and the sleeve 29. The sleeve of the cannula is sized so that when the obturator extends completely through it and beyond, insufflation fluid which passes through the stop-cock and the housing 28 can pass through an annular opening created by the slightly greater size of the internal diameter of the cannula sleeve in relation to the outer diameter of the hollow shaft of the obturator.

An obturator lock 26 is attached to the proximal end of the hollow shaft 24 of obturator 21. The obturator lock 26 has an opening therein (not shown) to enable the user to insert the endoscope 22 into and through the hollow shaft 24. When the endoscope is inserted through the hollow shaft of the obturator to a desired position, the position of the endoscope can be locked using latch 27. This locking assembly is described in detail in connection with co-pending application U.S. Ser. No. 08/382,461, filed Feb. 1, 1995, which is incorporated by reference herein. Optical obturator 21 can be secured to the cannula 23 when obturator lock 26 is latched onto the cannula housing 28.

A description of the surgical method for dissecting internal bodily tissue to create an operative space for the repair of a hernia will now be provided in conjunction with the sequence of steps illustrated in FIGS. 3–8. In each of FIGS. 3–8, there is illustrated the side of a surgical patient 31 with a portion of the patient's body from the umbilicus to the pubic bone exposed. For purposes of providing an easily definable reference, the umbilicus is designated in the figures as "UM" and the pubic bone as "PB". The exposed body portion also includes internal bodily tissue 32 composed of numerous adjacent layers of tissue designated as 32a, 32b, and 32c, respectively. The parietal peritoneum, which is designated as "PP", is one of the innermost layers of tissue, and provides protection for the internal bodily organs such as the intestines, much in the same way as the skin of a grapefruit protects the contents of the grapefruit from external trauma.

The object of the surgery is to create an operative space between the parietal peritoneum and the adjacent layers of internal bodily tissue at the region adjacent the pubic bone. Accordingly, an initial incision, which is designated as "I", is made adjacent the umbilicus with a scalpel to provide an initial passageway into the tissue. When the incision is made, the trocar assembly is inserted into the incision by directing the blunt tip 25 of the obturator 21 through the incision. Once the blunt tip of the trocar assembly has been inserted through the incision, the assembly is advanced through the tissue until the tip 25 of the optical obturator is positioned adjacent the parietal peritoneum. The advancement downwardly of the trocar assembly through the tissue can be observed visually using the endoscope 22 which transmits images relayed from the tissue through the transparent tip 25 of the optical obturator 21.

Figure 5:
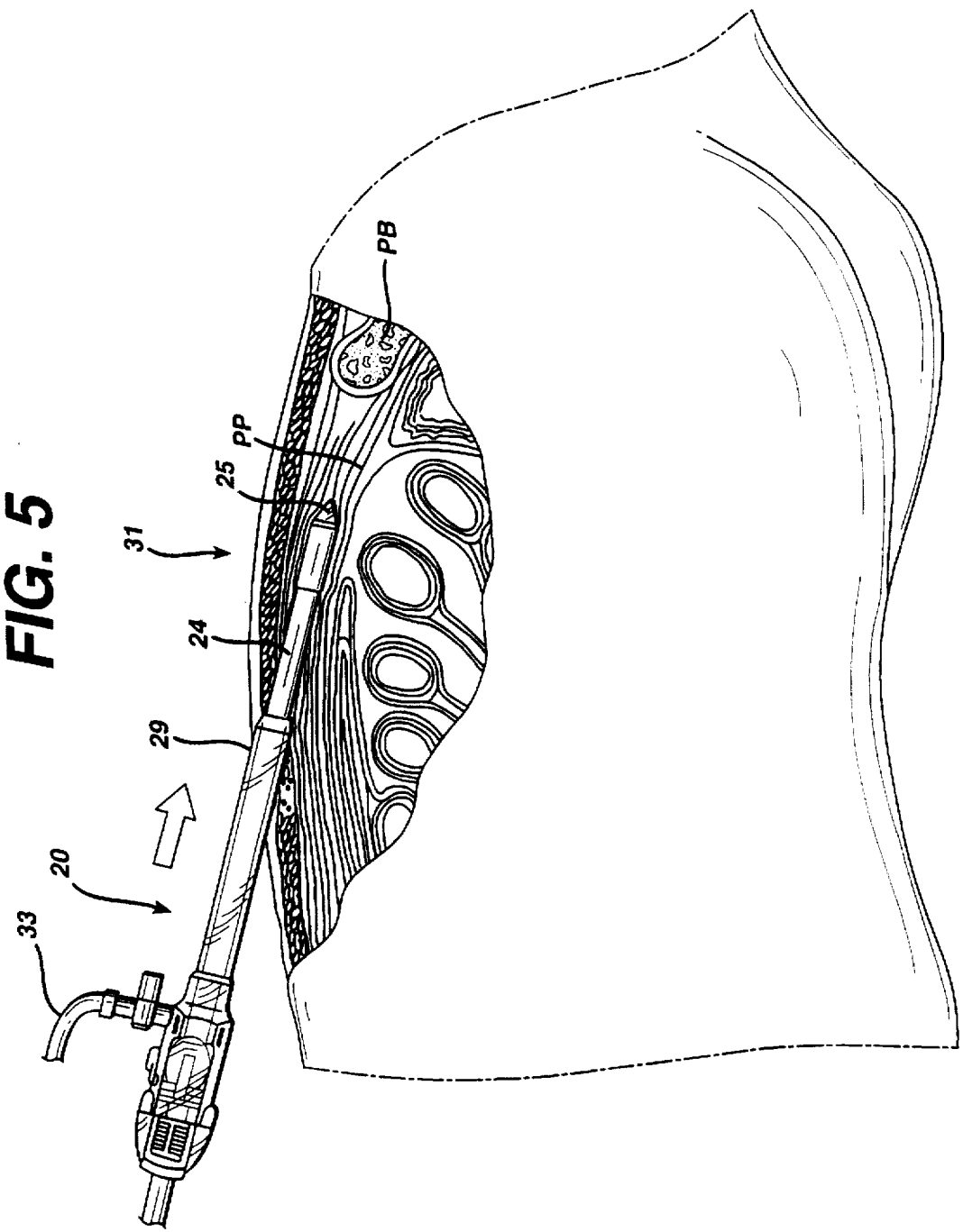
Figure 6:
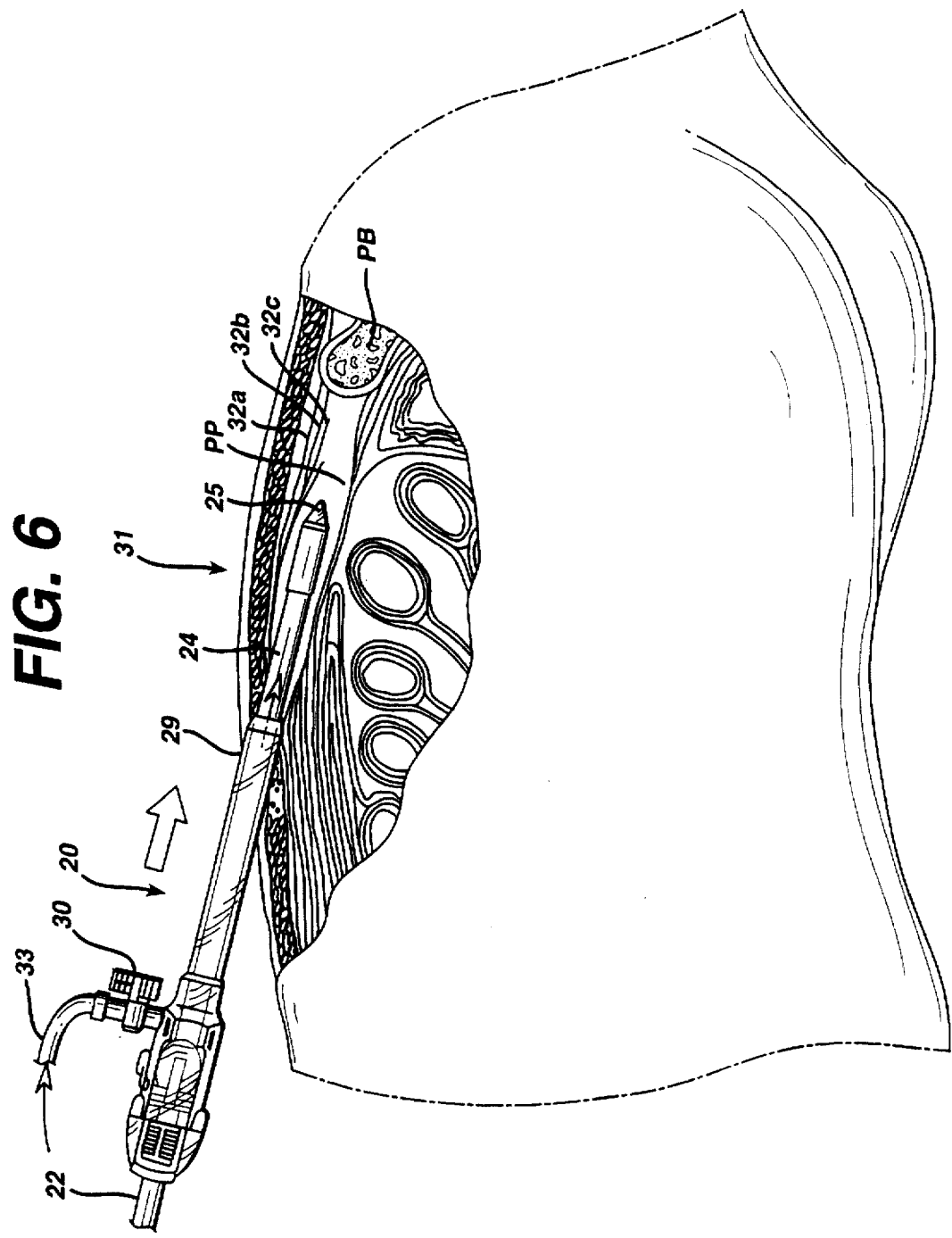

When the tip of the obturator is at or near the patient's parietal peritoneum, the assembly is then advanced generally in a direction parallel to the parietal peritoneum and the adjacent layers of internal bodily tissue 32a, 32b and 32c. As the trocar assembly is advanced, the parietal peritoneum is manually dissected away from the adjacent internal tissue layers. When the assembly has been advanced to a distance sufficient to advance the distal end of the cannula sleeve 29 through the incision and into the tissue, as illustrated in FIG. 5, the stop-cock valve on the cannula housing 28 can be turned on to allow the passage of the insufflation fluid through the sleeve 29. As illustrated in FIG. 6, the insufflation fluid passes in the direction indicated by the arrows through the flexible tubing, into the cannula housing 28, and into and out of the cannula sleeve 29. The insufflation fluid actually passes through the open annulus created between the difference in the inner diameter of the cannula sleeve 29 and the outer diameter of the elongated shaft 24 of the optical obturator. The insufflation fluid exits the distal end of the cannula sleeve, and provides insufflation at and around the layers of internal bodily tissue which are being manually dissected.

Figure 7:
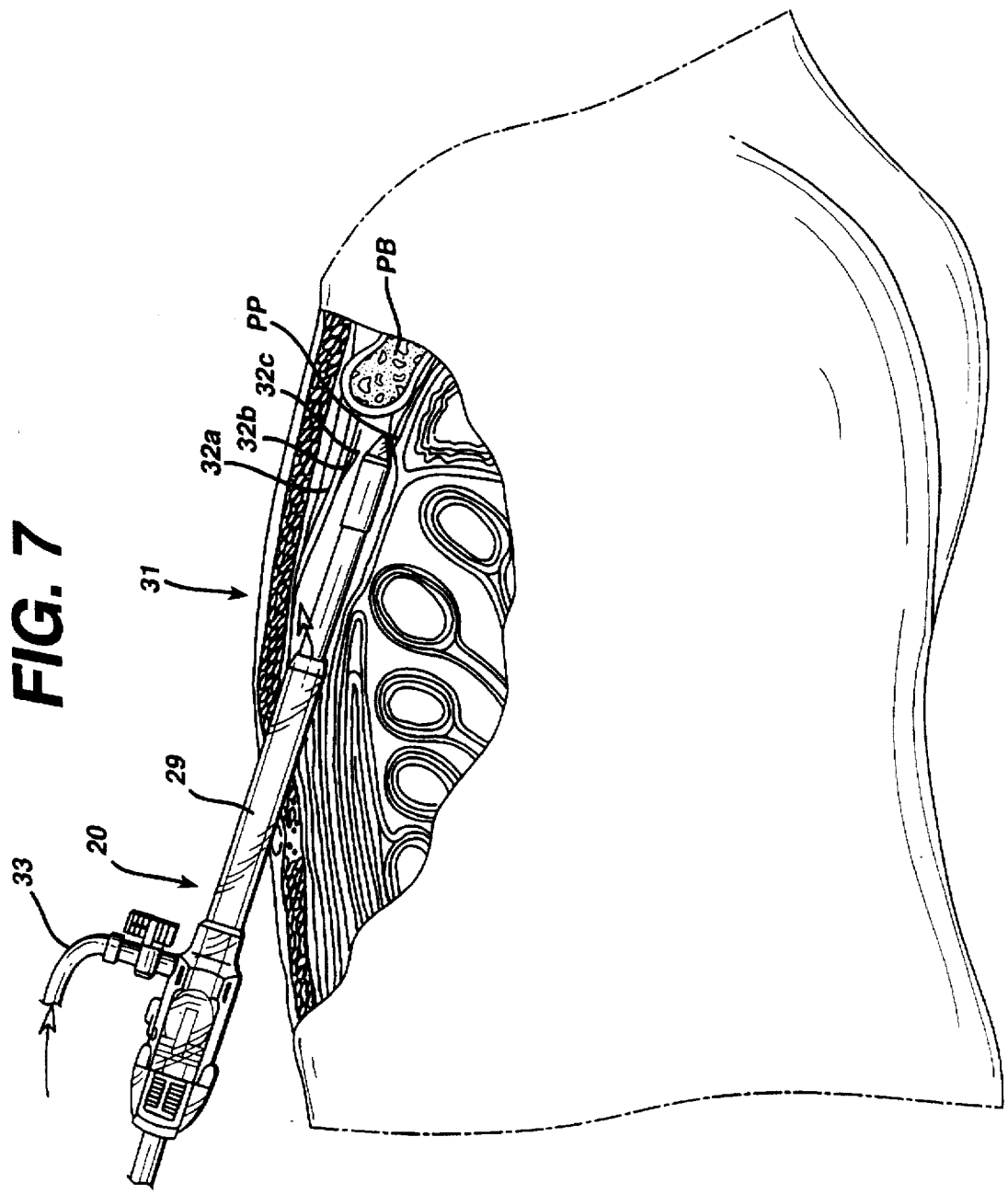
Figure 8:
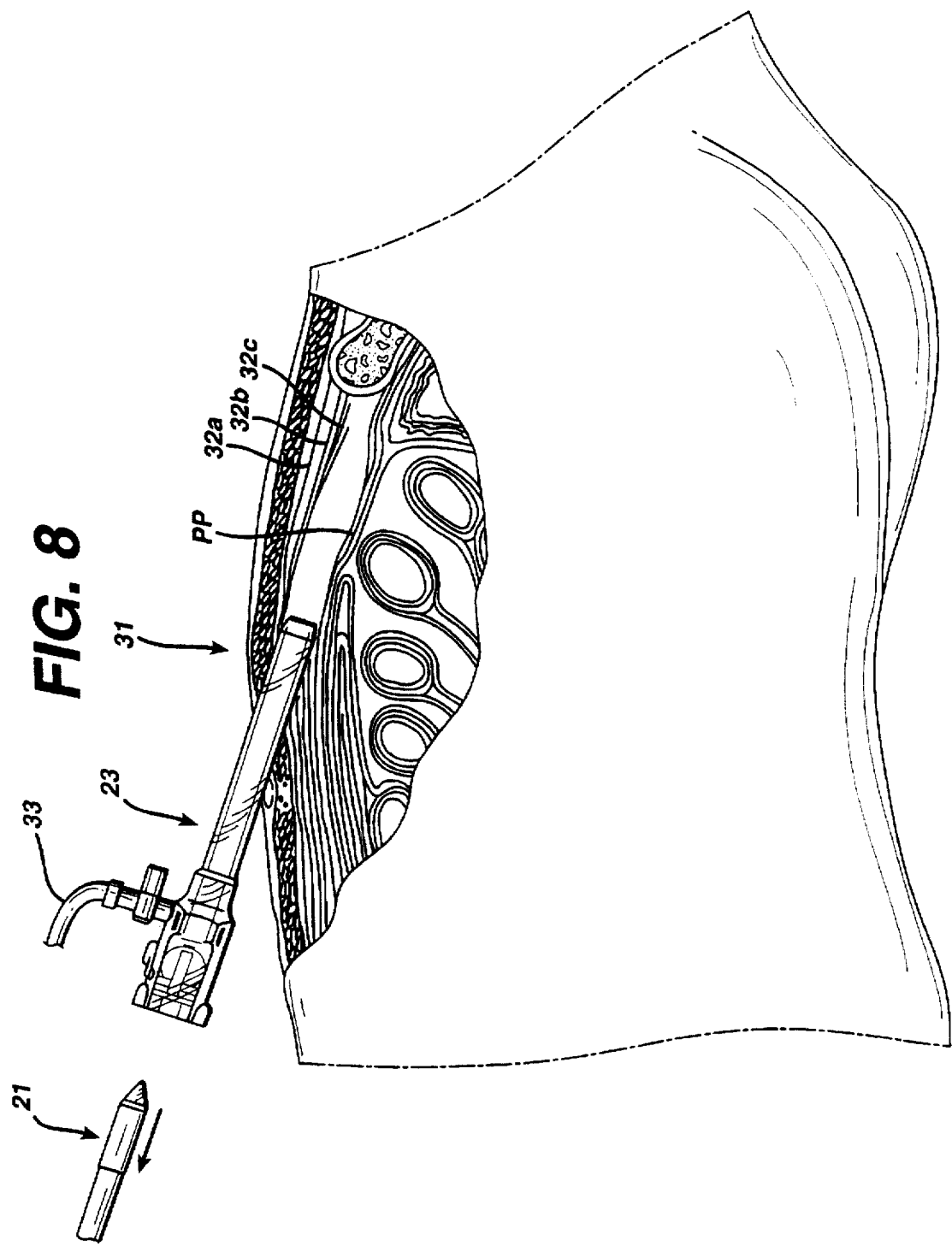

As illustrated, insufflation during the advance of the trocar assembly through the tissue further assists the manual dissection because the insufflation fluid facilitates the separation of the adjacent layers of tissue. As the insufflation is continued, the advancement of the trocar assembly under direct visualization is continued until the dissection is completed adjacent the pubic bone, which is illustrated in FIG. 7. Once the advancement is completed, the insufflation can be turned off and, as illustrated in FIG. 8, the obturator including the attached endoscope can be removed from the cannula. Accordingly, the cannula now provides a passageway for the insertion and withdrawal of surgical instruments necessary or desirable to repair the hernia within the operative space created adjacent the patient's parietal peritoneum at or near the pubic bone.

In another embodiment, it may be desirable or convenient to simply open the stop-cock valve on the trocar cannula at the outset of the surgical method and leave it on continuously during the procedure. In this way, it is unnecessary to remember to turn on the stop-cock during the surgery to provide the desired insufflation while the manual dissection is performed.

Figure 10:
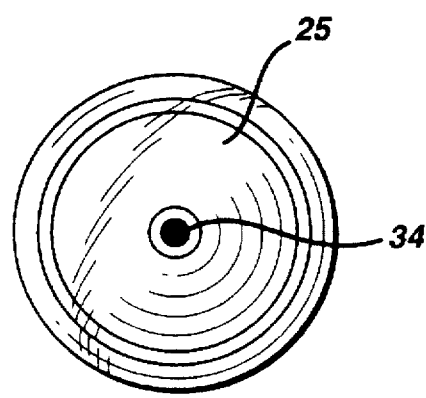
FIG. 10 is an end view of the surgical instrument as seen along view line 10—10 of FIG. 9.
Figure 11:
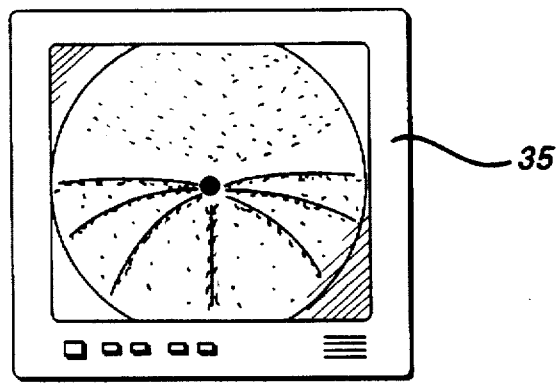
FIG. 11 is a schematic view of a video monitor showing the image of the operative space created between layers of internal tissue as illustrated in FIG. 7.

Another feature which is illustrated can be seen most particularly in FIGS. 10 and 11. A contrasting imaging element 34, preferably made from an indelible black ink or similar material in the form of a black dot, is placed at the apex of the transparent conical tip 25 of the obturator. This dot transects the longitudinal axis "L" of the elongated shaft 24 of the optical obturator, and provides a much desired orientation to the user as the instrument is advanced to dissect adjacent layers of tissue. As illustrated in FIG. 11, the dot 34 contrasts sharply with the illuminated images of the bodily tissue, and provides the user with visual information concerning the precise positioning of the tip 25 of the obturator as the assembly is advanced. This in turn enables the user to more precisely, quickly and confidently advance the assembly through the tissue to perform the manual dissection.

Although this invention has been described in connection with what the inventors perceive to be the most preferred embodiment, numerous additional embodiments will become apparent to those skilled in this field. For example, the relative difference in length between the cannula sleeve 29 and elongated shaft 24 can be shortened so that the distal end of the cannula sleeve is adjacent to the blunt tip 25 of the obturator. An insufflation fluid other than carbon dioxide, such as saline solution, can be used so that pressurized saline can exit the cannula sleeve adjacent the tip of the optical obturator to provide even greater assistance to separate the tissue as the trocar assembly is advanced during the manual dissection. Furthermore, an assembly providing for the introduction of saline may also desirably incorporate the ability to provide for suction of the saline introduced.

Another embodiment may include, for example, replacing the black dot as the contrasting imaging element 34 best illustrated in FIG. 10 with one or more contrasting lines intersecting the apex of the tip 25.

What is claimed is:

1. An improved surgical method for creating an operative space for performing a surgical procedure on a patient, the method having the steps of providing an instrument with an elongated shaft and a blunt tip at the shaft distal end, introducing the tip of the instrument adjacent to a first layer of internal bodily tissue desired to be dissected from adjacent layers of the tissue, and manually dissecting the first layer from the adjacent layers so as to create the operative space by advancing the instrument in a direction generally parallel to and between the first layer and the adjacent layers, wherein the improvement comprises:

insufflating the operative space with a pressurizing fluid concurrently with the step of manually dissecting so as to create an insufflated operative space; and removing the instrument from the patient after the insufflated operative space has been created for performing a surgical procedure within the insufflated operative space with another surgical instrument inserted into the insufflated operative space between the first layer and the adjacent layers of tissue.

2. The method of claim 1 wherein the instrument has an outer sleeve through which the shaft is inserted and the step of insufflating is carried out through the sleeve.

3. The method of claim 2 wherein the shaft of the instrument is hollow, at least a portion of the tip is transparent, an endoscope is received in the hollow shaft and extends adjacent to the tip, and the step of manually dissecting is carried out under direct visualization using the endoscope.

4. The method of claim 3 wherein the operative space is created at the patient's parietal peritoneum.

5. The method of claim 4 wherein the operative space is created to repair a hernia.

6. A surgical method for endoscopically dissecting internal bodily tissue so as to create an operative space remote from a point of entry for performing the surgical procedure on a patient, the method comprising:

providing a trocar assembly including a cannula having a cannula housing and an elongate cannula sleeve extending distally therefrom, and an obturator with a blunt tip slidably received into and through the cannula sleeve;

making an incision at the point of entry;

inserting the blunt tip of the trocar assembly through the incision until the tip contacts a desired layer of the internal bodily tissue;

advancing the tip in a direction generally parallel to the desired layer of the internal bodily tissue so as to dissect the layer from adjacent layers of the tissue while the cannula sleeve of the trocar assembly is likewise advanced;

insufflating at and around the dissected layer through the cannula sleeve with a pressurizing fluid while concurrently continuing to advance the blunt tip and sleeve of the trocar assembly toward a surgical site where the surgical procedure is to be performed so as to create an insufflated operative space;

removing the obturator after the insufflated operative space is created at the surgical site; and inserting another surgical instrument into the insufflated operative space between the first layer and the adjacent layers of tissue for performing the surgical procedure.

7. The method of claim 6 when the obturator is hollow, the blunt tip is a transparent window, the trocar assembly includes an endoscope inserted into the hollow obturator and extending to adjacent the transparent window, and the advancing step is carried out under direct visualization using the endoscope.

8. The method of claim 7 wherein the point of entry is adjacent the patient's umbilicus and the operative space created is at the patient's parietal peritoneum.

9. The method of claim 8 wherein the operative space is created to repair a hernia.

* * * * *